United States Patent [19]

Barner et al.

[11] Patent Number: 4,808,736

[45] Date of Patent: Feb. 28, 1989

[54] PROCESS FOR THE PREPARATION OF HYDROQUINONE DERIVATIVES AND D-α-TOCOPHEROL

[75] Inventors: Richard Barner, Witterswil; Josef Hübscher, Seon, both of Switzerland

[73] Assignee: Hoffmann-LaRoche Inc., Nutley, N.J.

[21] Appl. No.: 83,764

[22] Filed: Aug. 10, 1987

[30] Foreign Application Priority Data

Aug. 25, 1986 [CH] Switzerland ............... 3408/86

[51] Int. Cl.$^4$ ............... C07D 311/72; C07C 41/01
[52] U.S. Cl. ............... 549/408; 549/415; 549/214; 556/443; 568/592; 568/648
[58] Field of Search ............... 549/408, 415, 214; 568/648, 592; 556/443

[56] References Cited

U.S. PATENT DOCUMENTS

| | | | |
|---|---|---|---|
| 4,153,614 | 5/1979 | Barner et al. | 549/407 |
| 4,189,612 | 2/1980 | Cohen et al. | 568/763 |
| 4,424,389 | 1/1984 | Sakito | 568/648 X |
| 4,582,919 | 4/1986 | Barner et al. | 549/554 |
| 4,675,421 | 6/1987 | Barner et al. | 549/416 |
| 4,709,055 | 11/1987 | Barner et al. | 549/215 |

FOREIGN PATENT DOCUMENTS 0065368 11/1982 European Pat. Off. .

OTHER PUBLICATIONS

Meister, Ch. et al., Liebigs Ann. Chemie, (1983) 913-921.

*Primary Examiner*—Nicky Chan
*Attorney, Agent, or Firm*—Jon S. Saxe; Bernard S. Leon; William G. Isgro

[57] ABSTRACT

In this process of the invention a compound of the formula

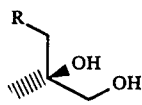

I wherein R is a leaving group, is reacted with a compound of the formula

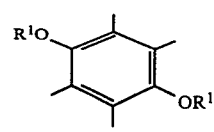

II wherein $R^1$ is an ether protecting group, and, if desired a thus-obtained compound of the formula

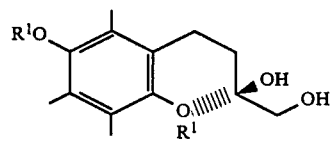

III is converted in a known manner into d-α-tocopherol.

6 Claims, No Drawings

PROCESS FOR THE PREPARATION OF HYDROQUINONE DERIVATIVES AND D-α-TOCOPHEROL

BRIEF DESCRIPTION OF THE INVENTION

The invention is relates to a process for the preparation of hydroquinone derivatives, which are suitable as intermediates for the preparation of d-α-tocopherol (natural vitamin E), and with a process for the preparation of d-α-tocopherol.

The invention comprises reacting a compound of the formula

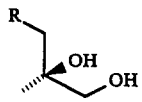
I wherein R is a leaving group,
with a compound of the formula

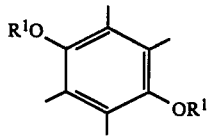
II wherein $R^1$ is an ether protecting group,
and, if desired, converting a thus-obtained compound of the formula

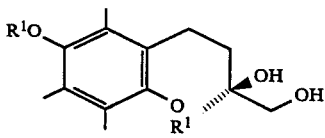
III wherein $R^1$ has the above significance,
into d-α-tocopherol.

DETAILED DESCRIPTION OF THE INVENTION

The present invention relates to a novel process for the preparation of hydroquinone derivatives, which are suitable as intermediates for the preparation of d-α-tocopherol (natural vitamin E), and with a process for the preparation of d-α-tocopherol.

Several processes for the preparation of natural vitamin E are known, but they are only of limited interest from the industrial point of view. Hitherto, natural vitamin E has been extracted almost exclusively from natural sources.

Accordingly, there exists a need for an industrially realizable process in accordance with which natural vitamin E can be obtained in good yield and with high optical purity. This is now possible by utilizing the process of the invention.

The process of the invention comprises reacting a compound of the formula

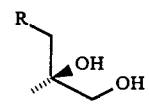
I wherein R is a leaving group,
with a compound of the formula

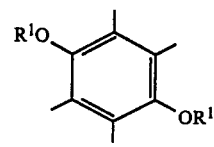
II wherein $R^1$ is an ether protecting group,
and, if desired, converting a thus-obtained compound of the formula

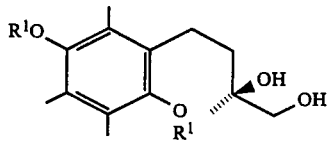
III wherein $R^1$ has the above significance,
into d-α-tocopherol.

The term "leaving group" denotes, in the scope of the present invention, not only a halogen such as chlorine, bromine or iodine, but also a sulfonic acid ester such as tosylate or mesylate and the like.

The term "ether protecting group" denotes in the scope of the present invention, not only groups which are cleavable by hydrolysis such as, for example, the silyl groups or alkoxymethyl groups, for example, methoxymethyl, or also tetrahydropyranyl, but also groups which are cleavable oxidatively such as, for example, $C_1$–$C_6$ alkyl ether groups. Furthermore, the notation " " denotes that the corresponding residue is situated above the plane of the molecule, while the notation " " denotes that the corresponding residue is situated below the plane of the molecule.

The reaction of a compound of formula I with a compound of formula II is conveniently effected by either heating a compound of formula I in an inert organic solvent with a compound of formula II in the presence of an alkali metal hydride or alkaline earth metal hydride and a phase transfer catalyst or as a first step reacting a compound of formula I in an inert organic solvent with an alkali metal hydride or alkaline earth metal hydride until the hydrogen evolution has ended and subsequently reacting the resulting product with a compound of formula II after the addition to the latter of a suitable alkali alkyl or alkaline earth alkyl compound in an inert organic solvent.

As inert organic solvents there can be used in the scope of the present invention the solvents which are conventionally used in metal-organic reactions. Examples of such solvents are ethers, especially cyclic ethers such as tetrahydrofuran or dioxane or also mixtures of these ethers with aliphatic hydrocarbons, such as pentane, hexane and the like. As alkali metal hydrides or alkaline earth metal hydrides, there can be used in the scope of the present invention, for example, lithium, sodium or potassium hydride or calcium hydride. The phase transfer catalysts required in the scope of the present invention are the customarily used, known phase transfer catalysts such as for example, quaternary ammonium salts, crown ethers or also polyethers and the like. As alkali alkyl or alkaline earth alkyl compounds there come into consideration in the scope of the present invention for example, tert. butyl lithium, $C_1$–$C_6$-alkyl potassium, Grignard compounds and the like.

The reaction of a compound of formula I with a compound of formula II in the presence of an alkali metal hydride or alkaline earth metal hydride and a phase transfer catalyst is carried out while heating to a temperature in the range of from about 60° C. to about the reflux temperature of the reaction mixture and optionally under pressure. In this reaction, there are used at least 3 moles of hydride per mol of a compound of formula I. The amount of phase transfer catalyst conveniently amounts in the range of from about 1 to about 10 mol%. The reaction of a compound of formula I with a compound of formula II in the absence of a phase transfer catalyst, that is, the reaction of a compound of formula I with an alkali metal hydride or alkaline earth metal hydride until the hydrogen evolution has ended as well as the reaction of a compound of formula II with a suitable alkali alkyl or alkaline earth alkyl compound and also the subsequent reaction, can be effected at a temperature in the range of from about −20° C. to +35° C., preferably at about room temperature. Lower temperatures are also possible, but are not convenient on economical grounds. In this reaction, there are used at least 2 moles of hydride per mol of a compound of formula I and 1 mol of alkali alkyl or alkaline earth alkyl compound per mol of a compound of formula II.

The compounds of formula III which are obtained according to the process of the invention are known and can be converted in a known manner into d-α-tocopherol.

The compounds of formulas I and II which are used as starting materials in the process of the invention are known compounds or analogs of known compounds which can be prepared in an analogs manner to the preparation of the known compounds.

EXAMPLE 1

2.4 g (19.6 mmol) of (2R)-2-methyl-3-chloropropane-1,2-diol and 4.28 g (22 mmol) of 2,5-dimethoxy-1,3,4,6-tetramethylbenzene were dissolved in 20 ml of dioxane and heated to reflux temperature within 1 hour with 1.27 g (66 mmol) of sodium hydride (80% in mineral oil) and 0.1 ml of polyethylene glycol 400 (as the phase transfer catalyst) and stirred at this temperature for 16 hours. The mixture was then treated with 50 ml of water, filtered and washed with water. The residue was recrystallized from ether/hexane and there were obtained 4.91 g of (2S)-2-methyl-4-(2,5-dimethoxy-3,4,6-trimethylphenyl)-1,2-butanediol in the form of white crystals with a melting point of 82°–84° C. and $[\alpha]_D^{20} = +2.86°$ (c=1.5% in CHCl$_3$).

EXAMPLE 2

A solution of 9.78 g (80 mmol) of (2R)-2-methyl-3-chloropropane-1,2-diol in 100 ml of tetrahydrofuran was reacted with 4.3 g (180 mmol) of sodium hydride at room temperature by the portionwise addition while stirring for 1 hour. To the suspension obtained there was added dropwise, while stirring at room temperature, a solution of 88 mmol of 2,5-dimethoxy-3,4,6-trimethylbenzyl lithium (obtained by reacting 17.2 g (88 mmol) of 2,5-dimethoxy-1,3,4,6-tetramethylbenzene in 20 ml of n-pentane with 88 mmol of tert.butyl lithium at room temperature) and the mixture was subsequently stirred at room temperature for an additional 16 hours. The mixture was then treated with 50 ml of water while stirring, the volatile constituents were removed by distillation in a vacuum (~15 mbar) and the separated material was removed by filtration and washed with water. The filter residue was recrystallized from ether/hexane and there were obtained 23 g of (2S)-2-methyl-4-(2,5-dimethoxy-3,4,6-trimethylphenyl)-1,2-butanediol in the form of white crystals with a melting point of 83°–85° C. and $[\alpha]_D^{20} = +2.86°$ (c=1.5% in CHCl$_3$).

The (2R)-2-methyl-3-chloropropane-1,2-diol used as the starting material was prepared as follows:

7.9 ml (26 mmol) of tetraisopropyl orthotitanate, 150 mg (2.5 mmol) of calcium hydride, 150 mg (2.5 mmol) of silica gel and 5 ml (30 mmol) of dibutyl D-tartrate were left to stand in 150 ml of methylene chloride at −18° C. for 10 minutes. Then, 1.16 ml (25 mmol) of beta-methallyl alcohol and 7 ml (50 mmol) of cumene hydroperoxide (66% in cumene) were added dropwise and the mixture was left to stand at −18° C. for 16 hours. Thereupon, 300 ml of ethyl ether and 50 ml (0.35 mol) of sodium hydroxide solution (28%) were added and the mixture was stirred at room temperature for 1.5 hours. The mixture was then extracted with ether, the organic phase was treated with 20.3 g (0.1 mol) of magnesium chloride and stirred at room temperature for 16 hours. The mixture was subsequently filtered, the filtrate was concentrated and cumene and cumene alcohol were removed by distillation with steam. The residue was concentrated and there were obtained 2.47 g of (2R)-2-methyl-3-chloropropane-1,2-diol as a colorless oil with $[\alpha]_D^{20} = -5.4°$ (c=3% in CHCl$_3$) and an optical purity of more than 98% (e.e.) according to the gas-chromatographical method (Mosher derivative).

We claim:

1. A process for the preparation of d-α-tocopherol which process comprises reacting a compound of the formula

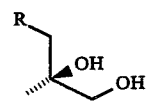

I wherein R is a leaving group, with a compound of the formula

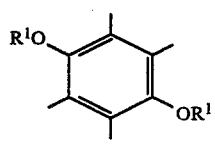

II wherein R$^1$ is an ether protecting group, in the presence of an alkali metal hydride or alkaline earth metal hydride and a phase transfer catalyst and, converting a thus-obtained compound of the formula

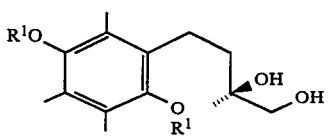

wherein R¹ is as described above into d-α-tocopherol.

2. A process according to claim 1, wherein the reaction of a compound of formula I with a compound of formula II is carried out in an inert organic solvent.

3. A process according to claim 2, wherein the reaction is carried out while heating to a temperature in the range of from about 60° C. to about the reflux temperature of the reaction mixture.

4. A process for the preparation of d-α-tocopherol which process comprises reacting a compound of the formula

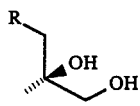

I wherein R is a leaving group
in an inert organic solvent with an alkali metal hydride or alkaline earth metal hydride until the hydrogen evolution ends and subsequently reacting the reaction product with a compound of the formula

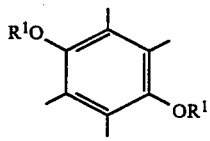

II wherein R¹ is an ether protecting group, after the addition to the latter of a suitable alkali alkyl or alkaline earth alkyl compound in an inert organic solvent.

5. A process according to claim 4, wherein the reaction is carried out at a temperature in the range of about −20° C. to about room temperature.

6. A process for the preparation of a hydroquinone derivative which comprises reacting a compound of the formula

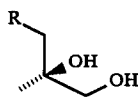

I wherein R is a leaving group,
with a compound of the formula

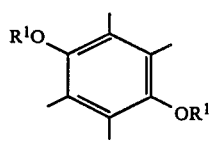

II wherein R¹ is an ether protecting group,
in the presence of an alkali metal hydride or alkaline earth metal hydride and a phase transfer catalyst and, recovering the resulting corresponding compound of the formula

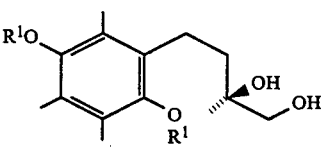

III wherein R¹ is as described.

* * * * *